United States Patent
Asai et al.

(10) Patent No.: US 11,319,405 B2
(45) Date of Patent: May 3, 2022

(54) CURING AGENT FOR WATER-BASED EPOXY RESIN, WATER-BASED EPOXY RESIN COMPOSITION, AND CURED PRODUCT THEREOF

(71) Applicant: MITSUBISHI GAS CHEMICAL COMPANY, INC., Tokyo (JP)

(72) Inventors: Yuiga Asai, Kanagawa (JP); Takuma Hanaoka, Kanagawa (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 20 days.

(21) Appl. No.: 16/343,325

(22) PCT Filed: Oct. 26, 2017

(86) PCT No.: PCT/JP2017/038651
§ 371 (c)(1),
(2) Date: Apr. 18, 2019

(87) PCT Pub. No.: WO2018/096868
PCT Pub. Date: May 31, 2018

(65) Prior Publication Data
US 2019/0256645 A1    Aug. 22, 2019

(30) Foreign Application Priority Data

Nov. 24, 2016 (JP) .............................. JP2016-228364

(51) Int. Cl.
C08G 59/50 (2006.01)
C07C 211/27 (2006.01)

(52) U.S. Cl.
CPC ........ *C08G 59/5033* (2013.01); *C07C 211/27* (2013.01); *C08G 59/5006* (2013.01)

(58) Field of Classification Search
CPC ............ C08G 59/5033; C08G 59/5006; C07C 211/27
USPC ....................................................... 523/402
See application file for complete search history.

(56) References Cited

U.S. PATENT DOCUMENTS

| | | |
|---|---|---|
| 5,344,856 A | 9/1994 | Klein |
| 5,670,612 A | 9/1997 | Kihara et al. |
| 2002/0055605 A1 | 5/2002 | Yonehamma et al. |
| 2009/0264593 A1 | 10/2009 | Volle et al. |
| 2015/0025178 A1 | 1/2015 | Jiang |
| 2016/0152522 A1* | 6/2016 | Wurmli ................ C08G 59/504 428/414 |

FOREIGN PATENT DOCUMENTS

| | | |
|---|---|---|
| CN | 104159946 | 11/2014 |
| EP | 1 452 554 | 9/2004 |
| EP | 3 441 385 | 2/2019 |
| JP | 60-168729 | 9/1985 |
| JP | 4-293953 | 10/1992 |
| JP | 8-127637 | 5/1996 |
| JP | 2001-502378 | 2/2001 |
| JP | 2002-161076 | 6/2002 |
| JP | 2002-361785 | 12/2002 |
| JP | 2005-28835 | 2/2005 |
| JP | 2007-197701 | 8/2007 |
| JP | 2007-197702 | 8/2007 |
| JP | 2008-503627 | 2/2008 |
| JP | 2008-280382 | 11/2008 |
| JP | 2010-539314 | 12/2010 |
| JP | 2012-153857 | 8/2012 |

OTHER PUBLICATIONS

Mitsubishi Gas Chemical Co., Inc., "Gaskamine240", 2020 (Year: 2020).*
Kuwahara et al., JP 2007-197701 A machine translation in English, Aug. 9, 2007 (Year: 2007).*
Huntsman, "Advanced Materials Waterborne systems", 2007 (Year: 2007).*
"Gaskamine 240 No. 02061H Ver. 2.0", Mitsubishi Gas Chemical Compnay, Inc., Feb. 2003.
Official Communication issued in InternationalApplication No. PCT/JP2017/038651, dated Jan. 23, 2018, and English translation thereof.

* cited by examiner

*Primary Examiner* — David T Karst
(74) *Attorney, Agent, or Firm* — Greenblum & Bernstein, P.L.C.

(57) ABSTRACT

A curing agent for a water-based epoxy resin, including a reaction composition (A) containing a reaction product of styrene and an amine compound represented by the following formula (1), a water-based epoxy resin composition containing the same, and a cured product thereof.

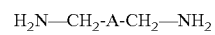

$$H_2N-CH_2-A-CH_2-NH_2 \quad (1)$$

wherein A is a 1,2-phenylene group, a 1,3-phenylene group, or a 1,4-phenylene group.

12 Claims, No Drawings

CURING AGENT FOR WATER-BASED EPOXY RESIN, WATER-BASED EPOXY RESIN COMPOSITION, AND CURED PRODUCT THEREOF

TECHNICAL FIELD

The present invention relates to a water-based epoxy resin curing agent, a water-based epoxy resin composition, and a cured product thereof.

BACKGROUND ART

A polyamine, and a compound obtained by subjecting a polyamine and an alkenyl compound, an epoxy compound, or the like to addition reaction are known to be useful as an epoxy resin curing agent. An epoxy resin composition using the epoxy resin curing agent has been widely used in the paint fields, such as a corrosion-resistant paint for ships, bridges, iron structures on land and sea, in the civil engineering construction fields, such as lining, reinforcement, crack repair materials, sealing materials, injection materials, primers, screeds, topcoats and FRP reinforcement of concrete structures, floor materials of buildings, lining of water supply and sewage systems, paving materials, and adhesives, in the electrical and electronic fields, such as die-attach materials and insulation sealants, and in the fiber reinforced plastic fields.

In the paint fields, solvent regulation has been recently strengthened in terms of environment and safety, so that studies on water-based production of paint have been underway. The water-based production of an epoxy resin-based paint is to use, for example, as a main agent, a water-based epoxy resin emulsified by adding an emulsifier and water to an epoxy resin.

PTL 1 discloses an epoxy curing reagent composition including an epichlorohydrin-metaxylylene diamine reaction product which does not substantially contain metaxylylene diamine, and at least one liquid hydroxyl-functional melting point depressant selected from the group including plasticizer alcohol and aqueous alcohol solvents, and a use of the epoxy curing reagent composition in combination with an epoxy resin aqueous dispersion.

PTL 2 discloses an aqueous primer composition containing at least one thermosetting, self-emulsifiable epoxy resin composition, at least one thermosetting, non-self-emulsifiable epoxy resin composition, water, and at least one curing agent, and discloses a nitrogen-containing compound having at least two amine functional groups as the curing agent. Further, as one of preferred nitrogen-containing compounds, a compound obtained by the reaction of xylylenediamine and epichlorohydrin, and the like are exemplified.

CITATION LIST

Patent Literature

PTL 1: JP 2001-502378 A
PTL 2: JP 2010-539314 A

SUMMARY OF INVENTION

Technical Problem

As disclosed in PTL 1 and PTL 2, as an epoxy resin curing agent used in combination with a water-based epoxy resin, a curing agent having high hydrophilicity has been typically used. However, a cured coating film prepared by using a water-based epoxy resin composition containing a water-based epoxy resin as a main agent and an epichlorohydrin-metaxylylene diamine reaction product as a curing agent is not sufficient in coating film performance such as water resistance, hardness, and appearance.

A problem to be solved by the present invention is to provide a water-based epoxy resin composition which does not contain a solvent, is also suitable in terms of environment or safety, has good curability, and is also excellent in coating film performance such as water resistance, hardness, and appearance; a cured product thereof, and a curing agent for a water-based epoxy resin, which is to be used with the water-based epoxy resin composition.

Solution to Problem

The present inventor has found that a curing agent for an epoxy resin, containing a curing agent component having a predetermined structure may solve the above problem.

The present invention relates to the following [1] to [14].

[1] A curing agent for a water-based epoxy resin, including a reaction composition (A) containing a reaction product of styrene and an amine compound represented by the following formula (1):

$$H_2N\text{—}CH_2\text{-}A\text{-}CH_2\text{—}NH_2 \quad (1)$$

wherein A is a 1,2-phenylene group, a 1,3-phenylene group, or a 1,4-phenylene group.

[2] The curing agent described in [1], wherein the reaction composition (A) contains 10% by mass or more of a compound represented by the following formula (2):

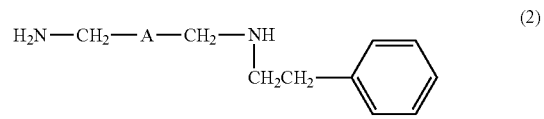

wherein A is the same as defined above.

[3] The curing agent described in [1] or [2], wherein A is a 1,3-phenylene group.

[4] The curing agent described in any one of [1] to [3], wherein a content of the reaction composition (A) in the curing agent is 30% by mass or more.

[5] The curing agent described in any one of [1] to [4], further including a reaction composition containing a reaction product of a compound having at least one epoxy group in a molecule thereof and a polyamine compound.

[6] The curing agent described in [5], wherein the reaction composition is a reaction composition (B) containing a reaction product of epichlorohydrin and the amine compound represented by the formula (1).

[7] The curing agent described in [6], wherein the reaction composition (B) contains, as a main component, a compound represented by the following formula (3):

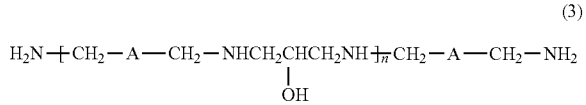

wherein A is the same as defined above, and n is a number of 1 to 12.

[8] The curing agent described in [5], wherein the reaction composition is a reaction composition (C) containing a reaction product of a compound having at least two epoxy groups in a molecule thereof and a polyamine compound.

[9] A water-based epoxy resin composition containing the curing agent described in any one of [1] to [8] and a water-based epoxy resin.

[10] The water-based epoxy resin composition described in [9], wherein the water-based epoxy resin is an epoxy resin emulsion containing an epoxy resin, an emulsifier, and water.

[11] The water-based epoxy resin composition described in [10], wherein an HLB of the emulsifier defined by a Griffin method is from 8.0 to 20.0.

[12] The water-based epoxy resin composition described in [10] or [11], wherein the emulsifier is one or more selected from the group consisting of polyoxyalkylene aryl ether and polyoxyalkylene alkyl aryl ether.

[13] A cured product of the water-based epoxy resin composition described in any one of [9] to [12].

[14] A curing agent mixture for a water-based epoxy resin, containing the curing agent described in any one of [1] to [8] and an emulsifier.

Advantageous Effects of Invention

By using the curing agent for a water-based epoxy resin of the present invention, it is possible to provide a water-based epoxy resin composition which does not contain a solvent, is also suitable in terms of environment or safety, has good curability, and is also excellent in coating film performance such as water resistance, hardness, and appearance. The water-based epoxy resin composition provides a cured product having good properties, and thus is suitably used for various paints such as a paint for corrosion resistance, an adhesive, a floor material, a sealant, a polymer cement mortar, a gas barrier coating, a primer, a screed, a topcoat, a sealing material, a crack repair material, a road paving material, and the like in addition to the use in a concrete material.

DESCRIPTION OF EMBODIMENTS

[Curing Agent for Water-Based Epoxy Resin]

A curing agent of the present invention is a curing agent for a water-based epoxy resin, and contains a reaction composition (A) (hereinafter, also simply referred to as "the reaction composition (A)") containing a reaction product of styrene and an amine compound represented by the following formula (1).

H₂N—CH₂-A-CH₂—NH₂ (1)

In the formula (1), A is a 1,2-phenylene group, a 1,3-phenylene group, or a 1,4-phenylene group.

The "water-based epoxy resin" in the present specification refers to an aqueous epoxy resin, or an epoxy resin usable in an aqueous dispersion state (emulsion).

The water-based epoxy resin will be described below, but as the water-based epoxy resin used in the present invention, an epoxy resin emulsion is preferred.

Hereinafter, each component constituting the curing agent of the present invention will be described.

<Reaction Composition (A)>

The curing agent of the present invention includes a reaction composition (A) containing a reaction product of styrene and the amine compound represented by the formula (1). A cured coating film of a water-based epoxy resin composition using a curing agent containing the reaction composition (A) has good water resistance, hardness, and appearance.

In the formula (1), A is preferably a 1,3-phenylene group or a 1,4-phenylene group, and more preferably a 1,3-phenylene group. That is, the amine compound represented by the formula (1) is one or more xylylenediamines selected from the group consisting of o-xylylenediamine, m-xylylenediamine (metaxylylenediamine; MXDA), and p-xylylenediamine (paraxylylenediamine; PXDA), preferably one or more selected from the group consisting of metaxylylenediamine and paraxylylenediamine, and more preferably metaxylylenediamine.

From the viewpoint of improving the water resistance, hardness, and appearance of a cured coating film of a water-based epoxy resin composition to be obtained, the reaction composition (A) contains a reaction product of styrene and the amine compound represented by the formula (1) in an amount of preferably 95% by mass or more, more preferably 98% by mass or more, and even more preferably 99% by mass or more. The upper limit thereof is 100% by mass.

Among them, it is preferred that the reaction composition (A) contains a compound represented by the following formula (2) in an amount of 10% by mass or more.

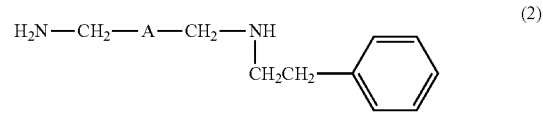

H₂N—CH₂—A—CH₂—NH
                    |
                    CH₂CH₂—⌬

(2)

In the formula (2), A is the same as defined above.

The compound represented by the formula (2) is, among reaction products of styrene and the amine compound (hereinafter, also referred to as "a raw material diamine" which are represented by the formula (1), a reaction product in which 1 mol of styrene and 1 mol of the raw material diamine are added to each other (hereinafter, also referred to as "a 1:1 adduct").

The reaction composition (A) may contain a multi-adduct such as a 2:1 adduct, a 3:1 adduct, and a 4:1 adduct of styrene and the raw material diamine in addition to a 1:1 adduct of styrene and the raw material diamine, which is the compound represented by the formula (2), but among the adducts, the 1:1 adduct of styrene and the raw material diamine has the lowest active hydrogen equivalent weight. The active hydrogen equivalent weight (hereinafter, also referred to as "AHEW") is a molecular weight per one equivalent of active hydrogen which may react with an epoxy resin which is a main agent of an epoxy resin composition. For this reason, a curing agent for a water-based epoxy resin using the reaction composition (A) including the compound represented by the formula (2) as a main component can exhibit good curing performance, even though an amount of curing agent for a water-based epoxy resin blended in the water-based epoxy resin composition is small.

From the viewpoint of obtaining the effect, the content of the compound represented by the formula (2) in the reaction composition (A) is more preferably 20% by mass or more, even more preferably 30% by mass or more, and still even more preferably 45% by mass or more. Further, the upper limit thereof is 100% by mass.

A content of the compound represented by the formula (2) in the reaction composition (A) may be obtained by a gas chromatography (GC) analysis.

An active hydrogen equivalent weight (AHEW) of the reaction composition (A) is preferably 130 or less, more preferably 120 or less, and even more preferably 110 or less. When the AHEW of the reaction composition (A) is 130 or less, the reaction composition (A) exhibits good curing performance even though the amount of curing agent blended in a water-based epoxy resin composition is small when the reaction composition (A) is used in a curing agent for a water-based epoxy resin. The AHEW of the reaction composition (A) is preferably 80 or more, and more preferably 90 or more from the viewpoint of ease of production, and the like.

The AHEW of the reaction composition (A) may be obtained, for example, by a titration method.

Further, a content of the amine compound represented by the formula (1) in the reaction composition (A) is preferably 5% by mass or less, more preferably 2% by mass or less, and even more preferably 1% by mass or less. When the content of the amine compound (raw material diamine) represented by the formula (1) in the reaction composition (A) is smaller, the water resistance or appearance of a cured coating film prepared by using a water-based epoxy resin composition in combination with a curing agent containing the reaction composition (A) is more improved.

The reaction composition (A) is obtained by subjecting styrene and the diamine represented by the formula (1) to addition reaction.

The addition reaction of styrene and the raw material diamine may be performed by a well-known method, and the method is not particularly limited, but it is preferred that the addition reaction is performed in the presence of a basic catalyst from the viewpoint of reaction efficiency. Examples of the basic catalyst include an alkali metal, an alkali metal amide (which is represented by formula MNRR' where M is an alkali metal, N is nitrogen, and R and R' are each independently hydrogen or an alkyl group), an alkylated alkali metal, and the like, and are preferably an alkali metal amide. Among them, as the basic catalyst, lithium amide ($LiNH_2$) is preferred.

In the addition reaction of styrene and the raw material diamine, an amount of basic catalyst used is preferably 0.1 to 20 mol %, more preferably 0.5 to 15 mol %, even more preferably 1.0 to 12 mol %, and still even more preferably 1.5 to 10 mol % based on 100 mol % of the total amount of the raw material diamine and styrene, which are used. When the amount of basic catalyst used is 0.1 mol % or more, the addition reaction rate is good, and when the amount of basic catalyst used is 20 mol % or less, the amount is economically advantageous.

For an amount of styrene and raw material diamine used in the addition reaction, from the viewpoint of obtaining the compound represented by the formula (2) at a high selectivity, a molar ratio of styrene to 1 mol of the raw material diamine ranges preferably from 0.1 to 5.0 mol, more preferably from 0.4 to 3.0 mol, even more preferably from 0.5 to 1.5 mol, and still even more preferably from 0.8 to 1.2 mol.

It is preferred that the addition reaction of styrene and the raw material diamine is performed by bringing the raw material diamine and a basic catalyst into contact with each other in advance to perform a preliminary reaction, and then adding styrene thereto. By performing the preliminary reaction, the activity of the raw material diamine is increased, and the addition reaction with the styrene is efficiently performed. The preliminary reaction of the raw material diamine and the basic catalyst may be performed, for example, by charging the raw material diamine and the basic catalyst into a reactor, and heating the mixture while stirring the mixture under an inert atmosphere such as a nitrogen gas.

The temperature at the time of the preliminary reaction of the raw material diamine and the basic catalyst is preferably 50 to 140° C., and more preferably 70 to 100° C. When the preliminary reaction temperature is 50° C. or more, the raw material diamine is sufficiently activated, so that the subsequent addition reaction is efficiently performed. In addition, when the preliminary reaction temperature is 140° C. or less, it is possible to avoid the heat deterioration and the like of the raw material diamine.

The time for the preliminary reaction is preferably 20 to 360 minutes, and more preferably 30 to 120 minutes. When the time for the preliminary reaction is 20 minutes or more, the raw material diamine is sufficiently activated, so that the subsequent addition reaction is efficiently performed. Furthermore, when the time is 360 minutes or less, the time is advantageous in terms of productivity.

The preliminary reaction of the raw material diamine and the basic catalyst is performed, and then styrene is added thereto to perform an addition reaction with the raw material diamine. The method for adding styrene is not particularly limited, but it is preferred that the styrene is added dividedly from the viewpoint of suppressing production of a polymeric product of styrene. Examples of the divided addition method include a method for adding styrene into a reactor by using a dropping funnel or a liquid feeding pump, and the like.

The temperature at the time of adding styrene, and at the time of the addition reaction is preferably 50 to 120° C., and more preferably 70 to 100° C. When the reaction temperature is 50° C. or more, the addition reaction of styrene and the raw material diamine is efficiently performed. Further, when the reaction temperature is 120° C. or less, it is possible to suppress production of a polymeric product of styrene, which is a byproduct.

In addition, the time for the addition reaction is not particularly limited, and may be appropriately selected according to the type of catalyst used, the reaction condition, and the like. For example, the time for the addition reaction may be set to a time until an amount of unreacted styrene becomes 1% by mass or less by performing a sampling of the reaction solution during the addition reaction, and performing the quantification of unreacted styrene with gas chromatography, liquid chromatography, or the like. Typically, the time for the addition reaction is preferably 10 to 180 minutes, and more preferably 20 to 120 minutes after the addition of styrene is completed. When the time for the addition reaction is 10 minutes or more, an amount of unreacted raw material remaining is small, and when the time for the addition reaction is 180 minutes or less, the time is advantageous in terms of productivity.

In the obtained reaction solution, a reaction product of styrene and the raw material diamine, and the basic catalyst are included. Further, unreacted raw material diamine and unreacted styrene are also included in some cases.

The basic catalyst may be removed by filtration, washing, adsorption, and the like according to the type thereof. For example, when the basic catalyst is an alkali metal amide, the alkali metal amide is changed into an easily removable salt by adding an acid such as hydrochloric acid, hydrogen chloride gas, and acetic acid, an alcohol such as methanol and ethanol, water, or the like thereto, and then the salt can be filtered. For example, when water is used, the alkali metal amide becomes a hydroxide, which is easily filtered.

After the basic catalyst is removed from the reaction solution as described above, a reaction composition (A) may be obtained by removing unreacted raw material diamine and unreacted styrene by distillation. By this operation, the content of the amine compound (raw material diamine) represented by the formula (1) in the reaction composition (A) may be preferably 1% by mass or less.

The content of the reaction composition (A) in the curing agent of the present invention is not particularly limited, but is preferably 30% by mass or more, more preferably 50% by mass or more, even more preferably 70% by mass or more, and still even more preferably 85% by mass or more from the viewpoint of obtaining the effect of the present invention. Further, the upper limit thereof is 100% by mass. When the content of the reaction composition (A) in the curing agent of the present invention is 30% by mass or more, the water resistance, appearance, and hardness of a cured coating film of a water-based epoxy resin composition using the curing agent become good.

<Other Curing Agent Components Other than Reaction Composition (A)>

The curing agent of the present invention may also include other curing agent components other than the reaction composition (A). Examples of the other curing agent components include a modified product of a polyamine compound, or a polyamine compound other than the amine compound (raw material diamine) represented by the formula (1) as a preferred component. The polyamine compound refers to a compound having at least two amino groups in the molecule thereof.

As the "the other curing agent components", a modified product of the polyamine compound or a reaction composition including the modified product is preferred from the viewpoint of obtaining a water-based epoxy resin composition having excellent coating film performance, such as water resistance, hardness, and appearance. Examples thereof include a reaction composition including a reaction product of a compound having at least one epoxy group in the molecule thereof and a polyamine compound. Among them, a reaction composition (B) including a reaction product of epichlorohydrin and the amine compound represented by the formula (1) (hereinafter, also simply referred to as "a reaction composition (B)"), or a reaction composition (C) including a reaction product of a compound having at least two epoxy groups in the molecule thereof and a polyamine compound (hereinafter, simply referred to as "a reaction composition (C)") is preferred.

<Reaction Composition (B)>

The curing agent of the present invention may also contain a reaction composition (B) including a reaction product of epichlorohydrin and the amine compound represented by the formula (1), as the other curing agent components other than the reaction composition (A). When a curing agent which also includes the reaction composition (B) is used as a curing agent for a water-based epoxy resin, a finger contact drying rate or curing rate of a coating film of the water-based epoxy resin composition is improved.

The amine compound represented by the formula (1) in the reaction composition (B) and preferred aspects thereof are the same as those described in the reaction composition (A).

It is preferred that the reaction composition (B) contains a compound represented by the following formula (3) as a main component. The "main component" as referred to herein refers to a component whose content is 50% by mass or more based on 100% by mass of the entire constituent components in the reaction composition (B):

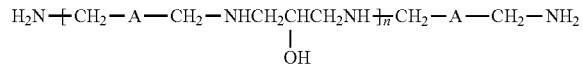

(3)

In the formula (3), A is the same as defined above. n is a number of 1 to 12.

A content of the compound represented by the formula (3) in the reaction composition (B) is preferably 60% by mass or more, more preferably 70% by mass or more, even more preferably 75% by mass or more, and still even more preferably 85% by mass or more. Further, the upper limit thereof is 100% by mass.

In addition, from the viewpoint of obtaining good curing performance as the curing agent, a compound having a high ratio of a compound with n=1 occupied in the compound represented by the formula (3) is preferred. A content of the compound with n=1 represented by the formula (3) in the reaction composition (B) is preferably 15% by mass or more, more preferably 20% by mass or more, and even more preferably 25% by mass or more.

The content of the compound represented by the formula (3) in the reaction composition (B) and the composition of the compound represented by the formula (3) may be obtained by a GC analysis and a gel permeation chromatography (GPC) analysis.

An active hydrogen equivalent weight (AHEW) of the reaction composition (B) is preferably 100 or less, more preferably 90 or less, and even more preferably 80 or less. When the AHEW of the reaction composition (B) is 100 or less, the reaction composition (B) exhibits higher curability even though the amount of reaction composition (B) blended in the water-based epoxy resin composition is small. The AHEW of the reaction composition (B) is preferably 45 or more, more preferably 50 or more, and even more preferably 60 or more, from the viewpoint of ease of production, and the like. The AHEW of the reaction composition (B) may be obtained by the method which is the same as defined above.

Furthermore, a content of the amine compound represented by the formula (1) in the reaction composition (B) is preferably 35% by mass or less, more preferably 28% by mass or less, even more preferably 5% by mass or less, and still even more preferably 1% by mass or less. When the content of the amine compound (raw material diamine) represented by the formula (1) in the reaction composition (B) is small, the water resistance or appearance of a cured coating film of a water-based epoxy resin composition obtained by using a curing agent including the reaction composition (B) is more improved.

The reaction composition (B) is obtained by subjecting epichlorohydrin and the diamine (raw material diamine) represented by the formula (1) to addition reaction.

The addition reaction of epichlorohydrin and the raw material diamine may be performed by a well-known method, and the method is not particularly limited, but it is preferred that the addition reaction is performed in the presence of a basic catalyst from the viewpoint of reaction efficiency. As the basic catalyst, an alkali metal hydroxide is preferred, one or more selected from the group consisting of potassium hydroxide and sodium hydroxide are more preferred, and sodium hydroxide is even more preferred. The alkali metal hydroxide may be used in a solid state or in an aqueous solution state, but it is more preferred that the alkali metal hydroxide is used in an aqueous solution state. A concentration of the aqueous alkali metal hydroxide solution is preferably within a range of 30 to 55% by mass.

In the addition reaction of epichlorohydrin and the raw material diamine, an amount of basic catalyst used is preferably approximately equimolar to epichlorohydrin, and preferably 0.7 to 2.0 mol, more preferably 0.8 to 1.5 mol, and even more preferably 0.9 to 1.2 mol, with respect to 1 mol of epichlorohydrin used.

For the amounts of epichlorohydrin and the raw material diamine used in the addition reaction, from the viewpoint of obtaining a compound with n=1 among the compounds represented by the formula (3) at a high selectivity, a molar ratio of the raw material diamine to 1 mol of epichlorohydrin ranges preferably from 1.5 to 12 mol, more preferably 1.5 to 6.0 mol, and even more preferably from 1.8 to 3.0 mol.

It is preferred that the addition reaction of epichlorohydrin and the raw material diamine is performed by mixing the raw material diamine and the basic catalyst in advance, and continuously adding epichlorohydrin thereto. For example, the addition reaction is performed by charging the raw material diamine and the basic catalyst in a reactor, heating the mixture while stirring the mixture under an inert atmosphere such as a nitrogen gas, and adding epichlorohydrin thereto. The method for adding epichlorohydrin is not particularly limited, but examples thereof include a method for adding epichlorohydrin into a reactor by using a dropping funnel or a liquid feeding pump, and the like.

The temperature at the time of adding epichlorohydrin is preferably 40 to 100° C. and more preferably 50 to 80° C. After the addition of epichlorohydrin is completed, the reaction temperature may be increased in order to improve the reaction efficiency, and the temperature at the time of the addition reaction is preferably 55 to 120° C. When the reaction temperature is 55° C. or more, the addition reaction of epichlorohydrin and the raw material diamine is efficiently performed.

The time for the addition reaction is not particularly limited, and typically, is preferably 10 minutes to 6 hours and more preferably 20 minutes to 4 hours after the addition of epichlorohydrin is completed. When the time for the addition reaction is 10 minutes or more, an amount of unreacted raw material remaining is small, and when the time for the addition reaction is 6 hours or less, the time is advantageous in terms of productivity.

After the reaction is completed, in an obtained reaction solution, a reaction product of epichlorohydrin and the raw material diamine, an unreacted raw material diamine, a basic catalyst, and water and a salt produced by the addition reaction are included. For the salt, for example, when an alkali metal hydroxide is used as the basic catalyst, an alkali metal chloride is produced.

The basic catalyst may be removed by filtration, washing, adsorption, and the like according to the type thereof. The water produced by the addition reaction may be removed, for example, under a reduced pressure condition at a temperature of 100° C. or less. Further, the salt produced by the addition reaction may be removed by filtration, and the like.

The reaction composition (B) may be obtained by removing the basic catalyst, water, and the salt from the reaction solution as described above. Further, an operation of removing unreacted raw material diamine may be carried out, if necessary. By this operation, the content of the amine compound (raw material diamine) represented by the formula (1) in the reaction composition (B) may be reduced.

When the curing agent of the present invention includes the reaction composition (B), the content thereof is preferably 1% by mass or more, more preferably 5% by mass or more, even more preferably 10% by mass or more, and still even more preferably 15% by mass or more. When the content thereof is within the range, it is possible to obtain an effect of adding the reaction composition (B). In addition, from the viewpoint of obtaining the water resistance and hardness of the cured coating film of the water-based epoxy resin composition, and from the viewpoint of lowering the viscosity, the content of the reaction composition (B) in the curing agent of the present invention is preferably 70% by mass or less, more preferably 50% by mass or less, and even more preferably 30% by mass or less.

<Reaction Composition (C)>

The curing agent of the present invention may also include a reaction composition (C) including a reaction product of a compound having at least two epoxy groups in the molecule thereof and a polyamine compound, as the other curing agent components other than the reaction composition (A). When a curing agent which also includes the reaction composition (C) is used as a curing agent for a water-based epoxy resin, a finger contact drying rate or water resistance of a coating film of the water-based epoxy resin composition becomes good.

Specific examples of the compound (hereinafter, also referred to as "a raw material epoxy compound") having at least two epoxy groups in the molecule thereof include butyl diglycidyl ether, neopentyl glycol diglycidyl ether, 1,3-propanediol diglycidyl ether, 1,4-butanediol diglycidyl ether, 1,6-hexanediol diglycidyl ether, biphenol diglycidyl ether, dihydroxy naphthalene diglycidyl ether, dihydroxy anthracene diglycidyl ether, triglycidyl isocyanurate, tetraglycidyl glycoluril, a polyfunctional epoxy resin having a glycidyl amino group derived from metaxylylene diamine, a polyfunctional epoxy resin having a glycidyl amino group derived from 1,3-bis(aminomethyl)cyclohexane, a polyfunctional epoxy resin having a glycidyl amino group derived from diaminodiphenylmethane, a polyfunctional epoxy resin having a glycidyl amino group derived from paraaminophenol, a polyfunctional epoxy resin having a glycidyloxy group derived from paraaminophenol, a polyfunctional epoxy resin having a glycidyloxy group derived from bisphenol A, a polyfunctional epoxy resin having a glycidyloxy group derived from bisphenol F, a polyfunctional epoxy resin having a glycidyloxy group derived from phenol novolac, a polyfunctional epoxy resin having two or more glycidyloxy groups derived from resorcinol, and the like. These compounds may be used either alone or in combination of two or more thereof. Furthermore, the "polyfunctional epoxy resin" refers to an epoxy resin having two or more epoxy groups in the molecule thereof.

In terms of finger contact drying rate or water resistance of a coating film of a water-based epoxy resin composition to be obtained, as a raw material epoxy compound, a compound including an aromatic ring or an alicyclic structure in the molecule thereof is more preferred, a compound including an aromatic ring in the molecule thereof is even more preferred, and a polyfunctional epoxy resin having a glycidyloxy group derived from bisphenol A is still even more preferred.

The polyamine compound used for producing the reaction composition (C) is not particularly limited as long as the polyamine compound is a compound having at least two amino groups in the molecule thereof. Examples thereof include 1,2-bis(aminomethyl)cyclohexane, 1,3-bis(aminomethyl)cyclohexane, 1,4-bis(aminomethyl)cyclohexane, o-xylylenediamine, m-xylylenediamine (MXDA), p-xylylenediamine (PXDA), menthenediamine, isophoronediamine (IPDA), diaminodicyclohexylmethane, bis(4-amino-3-methylcyclohexyl)methane, N-aminomethylpiperazine, norbornane diamine, bis(aminomethyl)tricyclodecane, ethylenediamine, diethylenetriamine, triethylenetetramine, tetraethylenepentamine, pentaethylenehexamine, polyoxyalkylene diamine, polyoxyalkylene triamine, and the like. These compounds may be used either alone or in combination of two or more thereof.

Among them, from the viewpoint of improving the finger contact drying rate or water resistance of the coating film of the water-based epoxy resin composition, as the polyamine compound used for producing the reaction composition (C), at least one selected from the group consisting of 1,2-bis(aminomethyl)cyclohexane, 1,3-bis(aminomethyl)cyclohexane, 1,4-bis(aminomethyl)cyclohexane, o-xylylenediamine, m-xylylenediamine (MXDA), p-xylylenediamine (PXDA), menthenediamine, and isophoronediamine (IPDA) is preferred, and isophoronediamine is more preferred.

From the viewpoint of improving the finger contact drying rate or water resistance of the coating film of the water-based epoxy resin composition, the reaction composition (C) contains a reaction product of a compound having at least two epoxy groups in the molecule thereof and a polyamine compound in an amount of preferably 30% by mass or more, more preferably 40% by mass or more, and even more preferably 45% by mass or more. The upper limit thereof is 100% by mass. In the reaction composition (C), a raw material epoxy compound or an unreacted polyamine compound other than the reaction product may be included.

An active hydrogen equivalent weight (AHEW) of the reaction composition (C) is preferably 200 or less, more preferably 125 or less, and even more preferably 115 or less. When the AHEW of the reaction composition (C) is 200 or less, the reaction composition (C) exhibits higher curability even though the amount of reaction composition (C) blended in the water-based epoxy resin composition is small. The AHEW of the reaction composition (C) is preferably 30 or more, and more preferably 60 or more from the viewpoint of ease of production, and the like. The AHEW of the reaction composition (C) may be obtained by the method which is the same as defined above.

The reaction composition (C) is obtained by subjecting the compound (the raw material epoxy compound) having at least two epoxy groups in the molecule thereof and the polyamine compound to addition reaction. The addition reaction may be performed by a well-known method, and the method is not particularly limited, but examples thereof include a method of charging a polyamine compound in a reactor, adding the raw material epoxy compound by a whole addition or a divided addition such as dropwise addition, and heating and reacting the mixture. It is preferred that the addition reaction is performed under an inert atmosphere such as a nitrogen gas.

From the viewpoint that the reaction composition (C) exhibits a function as a curing agent for an epoxy resin, it is preferred that in the addition reaction, an excessive amount of polyamine compound is used with respect to an epoxy equivalent weight of the raw material epoxy compound. Specifically, the raw material epoxy compound and the polyamine compound are used so as to become preferably [D]/[G]=50 to 4 and more preferably [D]/[G]=20 to 8 (here, [D] indicates the number of active hydrogens of the polyamine compound and [G] indicates the number of epoxy groups of the raw material epoxy compound). Within the range, the viscosity of the reaction composition (C) does not become excessively high, so that the handleability becomes excellent, and the curability of a water-based epoxy resin composition to be obtained and the performance of a cured coating film thereof also become good.

The temperature and the time for the reaction at the time of the addition reaction may be appropriately selected according to the types of raw material epoxy compound and polyamine compound used, and the like. From the viewpoint of the reaction rate and the productivity, and prevention of decomposition of the raw material, and the like, the temperature at the time of the addition reaction is preferably 50 to 150° C. and more preferably 70 to 120° C. Further, the time for the reaction is preferably 0.5 to 12 hours and more preferably 1 to 6 hours after the addition of the raw material epoxy compound is completed.

When the curing agent of the present invention includes the reaction composition (C), the content thereof is preferably 1% by mass or more, more preferably 5% by mass or more, even more preferably 10% by mass or more, and still even more preferably 20% by mass or more. When the content thereof is within the range, it is possible to obtain an effect of adding the reaction composition (C). In addition, from the viewpoint of lowering the viscosities of the curing agent and the water-based epoxy resin composition, the content of the reaction composition (C) in the curing agent of the present invention is preferably 95% by mass or less, more preferably 90% by mass or less, and even more preferably 60% by mass or less.

A well-known curing accelerator, a non-reactive diluent, a mercaptan-based curing agent or the like may also be blended with the curing agent of the present invention, within a range not impairing the effects of the present invention. Examples of the curing accelerator include tris (dimethylaminomethyl)phenol, benzyl alcohol, salicylic acid, triphenyl phosphite, styrenated phenol, bisphenol A, N,N-bis(3-(dimethylamino)propylurea, and mercaptan-terminated polysulfide compounds such as "Thiokol LP-3" (manufactured by Toray Fine Chemical Co., Ltd.).

However, the total content of the curing agent components (other curing agent components such as the reaction composition (A), the reaction composition (B), and the reaction composition (C)) in the curing agent of the present invention is preferably 70% by mass or more, more preferably 80% by mass or more, and even more preferably 90% by mass or more, from the viewpoint of obtaining the effect of the present invention. Further, the upper limit thereof is 100% by mass.

In addition, from the viewpoint of improving the water resistance or appearance of the cured coating film of the water-based epoxy resin composition, it is more preferred that the content of the diamine represented by the formula (1) in the curing agent of the present invention is small. The content is preferably 20% by mass or less, more preferably 5% by mass or less, and even more preferably 2% by mass or less.

An active hydrogen equivalent weight (AHEW) of the curing agent of the present invention is preferably 130 or less, more preferably 120 or less, and even more preferably 110 or less. When the AHEW of the curing agent is 130 or less, the curing agent exhibits high curability even though the amount of curing agent blended in the epoxy resin composition is small. Meanwhile, from the viewpoint of obtaining an excellent coating film performance such as water resistance, hardness, and appearance, the AHEW of the curing agent is preferably 65 or more and more preferably 70 or more.

The viscosity of the curing agent of the present invention at 25° C. is more preferably low from the viewpoint of handleability, and is preferably 2,500 mPa·s or less, more preferably 1,000 mPa·s or less, even more preferably 500 mPa·s or less, and still even more preferably 300 mPa·s or less. The lower limit of the viscosity is not particularly limited, but is preferably 10 mPa·s or more as the viscosity at 25° C. from the viewpoint of miscibility with the epoxy resin. The viscosity of the curing agent may be measured by an E-type viscometer, and specifically, the viscosity may be measured by the method in the Examples.

[Water-Based Epoxy Resin Composition]

The water-based epoxy resin composition of the present invention includes the above-described curing agent for a water-based epoxy resin of the present invention and a water-based epoxy resin. As described above, it is preferred that an epoxy resin emulsion is used as the water-based epoxy resin.

Examples of the epoxy resin emulsion include an epoxy resin emulsion in which an epoxy resin is emulsified and dispersed in water. As the epoxy resin, both a self-emulsifiable epoxy resin and a non-self-emulsifiable epoxy resin may be used.

When the non-self-emulsifiable epoxy resin is used, for example, an epoxy resin emulsion may be formulated by dispersing a non-self-emulsifiable epoxy resin in water in the presence of an emulsifier.

It is more preferred that a water-based epoxy resin used in the present invention is an epoxy resin emulsion containing an epoxy resin, an emulsifier, and water.

As the epoxy resin used in the epoxy resin emulsion, any epoxy resin may be used as long as the epoxy resin is an epoxy resin which has a glycidyl group reacting with an active hydrogen of the curing agent of the present invention, and may also be emulsified and dispersed in water. From the viewpoint of the water resistance or the hardness of a cured coating film of a water-based epoxy resin composition, an epoxy resin including an aromatic ring or an alicyclic structure in the molecule thereof is preferred.

Specific examples of the epoxy resin used in the epoxy resin emulsion include one or more resins selected from the group consisting of an epoxy resin having a glycidylamino group derived from metaxylylene diamine, an epoxy resin having a glycidylamino group derived from 1,3-bis(aminomethyl)cyclohexane, an epoxy resin having a glycidylamino group derived from diaminodiphenylmethane, an epoxy resin having a glycidylamino group derived from paraaminophenol, an epoxy resin having a glycidyloxy group derived from paraaminophenol, an epoxy resin having a glycidyloxy group derived from bisphenol A, an epoxy resin having a glycidyloxy group derived from bisphenol F, an epoxy resin having a glycidyloxy group derived from phenol novolac, and an epoxy resin having a glycidyloxy group derived from resorcinol.

Among them, from the viewpoint of the water resistance or the hardness of the cured coating film of the water-based epoxy resin composition, it is more preferred that the epoxy resin used in the epoxy resin emulsion includes, as a main component, one or more selected from the group consisting of an epoxy resin having a glycidylamino group derived from metaxylylene diamine, an epoxy resin having a glycidyloxy group derived from bisphenol A, and an epoxy resin having a glycidyloxy group derived from bisphenol F, it is even more preferred that the epoxy resin used in the epoxy resin emulsion includes, as a main component, one or more selected from the group consisting of an epoxy resin having a glycidyloxy group derived from bisphenol A and an epoxy resin having a glycidyloxy group derived from bisphenol F, and it is still even more preferred that the epoxy resin used in the epoxy resin emulsion includes, as a main component, an epoxy resin having a glycidyloxy group derived from bisphenol A. The "main component" as referred to herein means that other components may be included without departing from the gist of the present invention, and means preferably 50 to 100% by mass, more preferably 70 to 100% by mass, and even more preferably 90 to 100% by mass of the total components.

The epoxy resin used in the epoxy resin emulsion may be either a solid epoxy resin or a liquid epoxy resin. In the present invention, the "solid epoxy resin" means an epoxy resin which is a solid at room temperature (25° C.), and the "liquid epoxy resin" means an epoxy resin which is a liquid at room temperature (25° C.).

An epoxy equivalent weight of an epoxy resin used in an epoxy resin emulsion is preferably 150 g/equivalent weight or more from the viewpoint of the performance of a coating film of a water-based epoxy resin composition to be obtained, and is preferably 1,000 g/equivalent weight or less, and more preferably 800 g/equivalent weight or less from the viewpoint of the low viscosity or the curability of the water-based epoxy resin composition.

In the case of an epoxy resin emulsion in which an epoxy resin is dispersed in water in the presence of an emulsifier, it is preferred that an epoxy equivalent weight of a component (solid content) in which a dispersion medium is removed from the emulsion is also within the range.

The epoxy resins used in the epoxy resin emulsion may be used alone and may be used in combination of two or more thereof.

Further, an epoxy equivalent weight in an epoxy resin emulsion state is preferably 150 g/equivalent weight or more, more preferably 200 g/equivalent weight or more, even more preferably 300 g/equivalent weight or more, and still even more preferably 500 g/equivalent weight or more, from the viewpoint of the performance of a coating film of a water-based epoxy resin composition to be obtained, and is preferably 1,500 g/equivalent weight or less from the viewpoint of the low viscosity or the curability of the water-based epoxy resin composition.

The concentration of the epoxy resin in the epoxy resin emulsion is not particularly limited, but is preferably 40% by mass or more and more preferably 50% by mass or more, and typically 80% by mass or less.

For the emulsifier used in the epoxy resin emulsion, an HLB defined by the Griffin method is preferably 8.0 to 20.0, more preferably 10.0 to 20.0, and even more preferably 12.0 to 20.0. When the HLB of the emulsifier is within the range, the epoxy resin is easily emulsified in water, and a cured coating film of a water-based epoxy resin composition to be obtained becomes excellent in performance of the coating film such as water resistance, hardness, and appearance.

Here, an HLB (Hydrophile-Lypophile Balance) is a value showing the affinity in water and oil which are an emulsifier, and may be obtained from the following equation by the Griffin method.

$$\text{HLB} = 20 \times [(\text{a molecular weight of a hydrophilic group included in an emulsifier})/(\text{a molecular weight of the emulsifier})]$$

As the emulsifier used in the epoxy resin emulsion, it is possible to use any of a nonionic emulsifier, an anionic emulsifier, a cationic emulsifier, an amphoteric emulsifier, and a reactive group-containing emulsifier having a reactive group. From the viewpoint that the selection range of the curing agent is wide, one or more selected from the group consisting of a nonionic emulsifier, an anionic emulsifier, and a reactive group-containing emulsifier are preferred, and a nonionic emulsifier is more preferred.

Examples of the nonionic emulsifier include a polyether-based compound, an ester-based compound, an alkanol-amide-based compound, and the like. Among them, a polyether-based compound is preferred, and a nonionic compound having a polyoxyalkylene structure is more preferred.

Examples of the nonionic compound having a polyoxyalkylene structure include: a polyalkylene glycol or polyalkylene glycol copolymer such as polyethylene glycol, polypropylene glycol, and polyoxyethylene polyoxypropylene glycol; a polyoxyalkylene alkyl ether such as polyoxyethylene myristyl ether and polyoxyethylene octyl dodecyl ether; a polyoxyalkylene aryl ether such as polyoxyethylene phenyl ether, polyoxyethylene styrenated phenyl ether, polyoxyethylene naphthyl ether, polyoxyethylene bisphenol A ether, and polyoxyethylene bisphenol F ether; a polyoxyalkylene alkyl aryl ether such as polyoxyethylene benzyl ether and polyoxyethylene dodecyl phenyl ether; and the like.

Among them, from the viewpoint that an epoxy resin is easily emulsified in water, and the performance of the coating film such as water resistance, hardness, and appearance of a cured coating film of a water-based epoxy resin composition to be obtained becomes good, one or more selected from the group consisting of polyoxyalkylene aryl ether and polyoxyalkylene alkyl aryl ether are preferred, one or more selected from the group consisting of polyoxyethylene aryl ether and polyoxyethylene alkyl aryl ether are more preferred, polyoxyethylene aryl ether is even more preferred, and polyoxyethylene styrenated phenyl ether is still even more preferred.

Preferred examples of the nonionic emulsifier that may be used in the epoxy resin emulsion include commercially available products such as NOIGEN series and Epan series manufactured by Daiichi Kogyo Seiyaku Co., Ltd., and BLAUNON series manufactured by Aoki Oil Industrial Co., Ltd.

Examples of the anionic emulsifier include: alkylsulfates such as sodium lauryl sulfate; polyoxyethylene alkyl ether sulfates such as sodium polyethoxyethylene lauryl ether sulfate; alkyl aryl sulfonates such as alkyl benzene sulfonate; alkane sulfonates; fatty acid salts such as sodium laurate; polyoxyethylene alkyl ether carboxylates such as polyoxyethylene alkyl ether acetate; sulfosuccinates such as dialkyl sulfosuccinate; and the like.

Examples of the cationic emulsifier include alkylamine salts, alkyl quaternary ammonium salts, and the like. In addition, examples of the amphoteric emulsifier include alkyl betaine-based compounds such as alkyl dimethylaminoacetic acid betaine, fatty acid amidopropyl betaine, and alkyl hydroxy sulfobetaine, and the like.

Examples of the reactive group-containing emulsifier include an epoxy group, a vinyl group, and the like. From the viewpoint that the performance of the coating film such as water resistance, hardness, and appearance of a cured coating film of a water-based epoxy resin composition to be obtained becomes good, as the reactive group-containing emulsifier used in the present invention, an epoxy group-containing emulsifier is preferred.

Preferred examples of the epoxy group-containing emulsifier include an epoxy group-containing polymer such as an acrylic polymer having an epoxy group and an acryl-styrene-based polymer having an epoxy group.

An epoxy equivalent weight of the epoxy group-containing emulsifier is preferably 150 to 4,000 g/equivalent weight, more preferably 300 to 2,000 g/equivalent weight, and even more preferably 300 to 1,500 g/equivalent weight.

Preferred examples of the epoxy group-containing emulsifier which may be used in the epoxy resin emulsion include commercially available products such as MARPROOF series manufactured by NOF Corporation and Alpha Resin series "W-10" and "W-12" manufactured by Alpha-Kaken Co., Ltd.

The emulsifiers may be used either alone or in combination of two or more thereof.

Among the emulsifiers, one or more selected from the group consisting of polyoxyalkylene aryl ether and polyoxyalkylene alkyl aryl ether having an HLB of 12.0 to 20.0 defined by the Griffin method are preferred, one or more selected from the group consisting of polyoxyethylene aryl ether and polyoxyethylene alkyl aryl ether having an HLB of 12.0 to 20.0 are more preferred, polyoxyethylene aryl ether having an HLB of 12.0 to 20.0 is even more preferred, and polyoxyethylene styrenated phenyl ether having an HLB of 12.0 to 20.0 is still even more preferred.

The content of the emulsifier in the epoxy resin emulsion is preferably 0.1 to 40 parts by mass, more preferably 0.5 to 30 parts by mass, and even more preferably 1 to 20 parts by mass based on 100 parts by mass of the epoxy resin. Based on 100 parts by mass of the epoxy resin, when the emulsifier is included in an amount of 0.1 parts by mass or more, the emulsion stability of the epoxy resin is good, and when the emulsifier is included in an amount of 40 parts by mass or less, it is possible to maintain the good water resistance, hardness, appearance, and the like of a cured coating film of a water-based epoxy resin composition to be obtained.

The epoxy resin emulsion which is a water-based epoxy resin may contain components other than the epoxy resin, the emulsifier, and water, and the total content of the epoxy resin, the emulsifier, and water is preferably 70% by mass or more, more preferably 80% by mass or more, and even more preferably 90% by mass or more, and the upper limit thereof is 100% by mass.

Examples of a commercially available epoxy resin emulsion which may be used as a water-based epoxy resin include commercially available products, such as "W2801", "W2821R70", "W3435R67", "W8735R70", "W1155R55", and "W5654R45", which are jER series manufactured by Mitsubishi Chemical Corporation, "EM-101-50" manufactured by ADEKA Corporation, "EPICLON EXA-8610" manufactured by DIC Corporation, "PZ 3901", "PZ 3921", and "PZ 3961-1", which are Araldite series manufactured by Huntsman Advanced Materials, Inc., "DER 915" and "DER 917" manufactured by Olin Corporation, and "Resin 3520-WY-55" and "Resin 6520-WH-53", which are EPIREZ series manufactured by Hexion Specialty Chemicals.

The content of the curing agent in the water-based epoxy resin composition of the present invention is an amount in which the ratio of the number of active hydrogens in the curing agent to the number of epoxy groups in the water-based epoxy resin is preferably 1/0.8 to 1/1.2, more preferably 1/0.9 to 1/1.1, and even more preferably 1/1.

In the water-based epoxy resin composition of the present invention, a modifying component such as a filler and a plasticizer, a flow control component such as a thixotropic agent, and other components such as a pigment, a leveling agent, a tackifier may also be included according to the use.

A preparation method of the water-based epoxy resin composition of the present invention is not particularly limited, and the curing agent, the water-based epoxy resin, and other components, if necessary, may be mixed and prepared by using well-known methods and apparatuses.

When an epoxy resin emulsion containing an epoxy resin as the water-based epoxy resin, an emulsifier, and water is used, a water-based epoxy resin composition may be formulated by firstly blending and mixing the curing agent with the epoxy resin and the emulsifier which are raw materials for the epoxy resin emulsion, continuously adding water thereto dividedly, and mixing the mixture. By this operation, it is possible to emulsify and disperse the epoxy resin in water, and simultaneously formulate a water-based epoxy resin composition, so that it is possible to obtain a composition having a good dispersed state of the epoxy resin.

The content of water in the water-based epoxy resin composition of the present invention is 10% by mass or more, preferably 15% by mass or more, and more preferably 20% by mass or more. The upper limit of the content of water may be appropriately adjusted according to the concentration of the water-based epoxy resin composition, but is typically 80% by mass or less, and preferably 60% by mass or less.

Further, it is preferred that the water-based epoxy resin composition of the present invention does not contain an organic solvent, and the content thereof is preferably 10% by mass or less, more preferably 5% by mass or less, and even more preferably 2% by mass or less.

<Curing Agent Mixture for Water-Based Epoxy Resin>

A curing agent mixture for a water-based epoxy resin of the present invention (hereinafter, also simply referred to as "the curing agent mixture") includes the above-described curing agent for a water-based epoxy resin of the present invention and the emulsifier. By blending and mixing the curing agent mixture with the epoxy resin and water, it is possible to easily formulate a water-based epoxy resin composition containing an epoxy resin emulsified and dispersed in water and a curing agent for a water-based epoxy resin.

The emulsifier used in the curing agent mixture is used without particular limitation as long as the emulsifier may emulsify and disperse the used epoxy resin in water, and the same emulsifier as used in the above-described epoxy resin emulsion may be used.

The mass ratio of the curing agent for a water-based epoxy resin to the emulsifier in the curing agent mixture is also not particularly limited and may be selected according to the AHEW of the curing agent, the type of emulsifier, and the like, but the mass ratio of the curing agent for a water-based epoxy resin to the emulsifier is typically within a range of 5/95 to 99.9/0.1 and preferably within a range of 10/90 to 99/1.

The curing agent mixture may include components other than the curing agent for a water-based epoxy resin of the present invention and the emulsifier, but the total content of the curing agent and the emulsifier is preferably 70% by mass or more, more preferably 80% by mass or more, and even more preferably 90% by mass or more, and the upper limit thereof is 100% by mass.

<Use>

The water-based epoxy resin composition of the present invention may exhibit excellent performance of the coating film such as water resistance, hardness, and appearance, and thus is suitably used for various paints such as a paint for corrosion resistance, an adhesive, a floor material, a sealant, a polymer cement mortar, a gas barrier coating, a primer, a screed, a topcoat, a sealing material, a crack repair material, a road paving material, and the like in addition to the use in a concrete material.

[Cured Product]

A cured product of the water-based epoxy resin composition of the present invention (hereinafter, also simply referred to as "the cured product of the present invention") is a cured product obtained by curing the above-described water-based epoxy resin composition of the present invention by a well-known method. The curing conditions of the water-based epoxy resin composition are appropriately selected according to the use and the form, and are not particularly limited.

The form of the cured product of the present invention is also not particularly limited, and may be selected according to the use. For example, when the water-based epoxy resin composition is used as a topcoat or primer of a concrete material, or for various paints, a cured product of the water-based epoxy resin composition is typically a film-like cured product. When the cured product of the present invention is a film-like cured product, the cured product is preferred in that the excellent performance of the coating film may be exhibited.

EXAMPLES

Hereinafter, the present invention will be described in detail with reference to Examples and Comparative Examples, but the present invention is not limited to the following Examples. Further, the curing agent for a water-based epoxy resin and the water-based epoxy resin composition were evaluated by the following methods.

(Calculation of Active Hydrogen Equivalent Weight (AHEW))

Among the curing agents for a water-based epoxy resin in each example, the active hydrogen equivalent weight (AHEW) of the curing agent composed of two curing agent components (reaction composition) was calculated by the calculation formula to be described below.

When an AHEW of a curing agent obtained by mixing a reaction composition having an AHEW of X and a reaction composition having an AHEW of Y at a mass ratio of A:B is Z, $$Z=[(A+B)XY]/(AY+BX).$$

(Content of Metaxylylenediamine)

The content of metaxylylenediamine in a curing agent for a water-based epoxy resin (or a curing agent solution) and constituent components thereof was measured by gas chromatography.

(Measurement of Viscosity)

The viscosity of the curing agent for a water-based epoxy resin (or the curing agent solution) at 25° C. was measured by using an E-type viscometer "TVE-22H type viscometer cone plate type" (manufactured by Told. Sangyo Co., Ltd.).

(Curing Rate)

The water-based epoxy resin composition in each example was applied onto a glass plate (manufactured by Taiyu Machinery Co., Ltd., 25×348×2.0 mm) under the conditions of 23° C. and 50% R.H., by using an applicator of 76 μm, thereby forming a coating film. The glass plate on which the coating film was formed was set on a paint drying time measuring instrument (manufactured by Taiyu Machinery Co., Ltd.), the striations when the needle of the measuring instrument scratched the surface of the coating film were observed, and the time to reach each drying step (Set to Touch, Dust Free, and Dry Through) was measured according to the following criteria. A shorter time indicates a higher curing rate.

Set to Touch: time taken until when traces of the needle start to remain in the glass plate shape Dust Free: time taken until when the needle emerges from the middle of the coating film onto the surface of the coating film Dry Through: time taken until when no traces of the needle remain on the coating film (Finger Contact Drying)

According to the following test conditions 1 and 2, the water-based epoxy resin composition in each example was applied onto a substrate using an applicator to form a coating film. This coating film was kept under the conditions of 23° C. and 50% R.H., and after 1, 2, and 7 days passed, the coating film was evaluated by finger contact according to the following criteria.

Ex: Excellent (even when the coating film is pressed down with the thumb at a force of 50 N), there is no stickiness of the coating film and no fingerprint remains)

G: Good (when the coating film is pressed down with the thumb is pressed at a force of 50 N, there is no stickiness of the coating film, but there is a remaining fingerprint after the finger contact)

F: Fair (when the coating film is pressed down with the thumb at a force of 50 N, there is a stickiness of the coating film)

P: Poor (when the coating film is pressed down with the thumb at a force of 5 N, there is a stickiness of the coating film)

[Test Condition 1]

Substrate: Zinc phosphate-treated iron plate (manufactured by Paltech Co., Ltd.; SPCC-SD PB-N144 0.8×70×150 mm)

Coating film thickness immediately after coating: 200 μm

[Test Condition 2]

Substrate: Fiber-reinforced cement board (JIS A5430: 2013)

Coating film thickness immediately after coating: 100 μm

Further, the test condition 1 is an evaluation condition which is stricter than the test condition 2. The reason is that water in the coating film easily volatilizes because the thickness of the coating film is small and the substrate is well-drained in the test condition 2 as compared to in the test condition 1.

(Water Resistance Spot Test)

According to the test conditions 1 and 2, the water-based epoxy resin composition in each example was applied onto a substrate using an applicator to form a coating film. This coating film was kept under the conditions of 23° C. and 50% R.H., and after 1, 2, and 7 days passed, 2 to 3 drops of pure water were dropped on the surface of the coating film with a dropper, and the portion was covered with a 50 mL screw tube bottle. After 24 hours passed, water was wiped off, and the appearance was observed visually and evaluated according to the following criteria.

Ex: Excellent (there is no change at all)

G: Good (there is a slight change, but there is no problem with use)

F: Fair (there is slight whitening)

P: Poor (whitening)

(Pencil Hardness)

According to the test conditions 1 and 2, the water-based epoxy resin composition in each example was applied onto a substrate using an applicator to form a coating film. This coating film was kept under the conditions of 23° C. and 50% R.H., and after 1, 2, and 7 days passed, the pencil hardness was measured in accordance with JIS K5600-5-4: 1999.

(Appearance of Coating Film)

According to the test condition 1, the water-based epoxy resin composition in each example was applied using an applicator under the conditions of 23° C. and 50% R.H. to form a coating film. The appearance of the coating film obtained one week after the painting was observed visually to evaluate glossiness, transparency, and smoothness according to the following criteria.

<Glossiness>

Ex: Excellent (there is gloss)

G: Good (gloss slightly deteriorates, but there is no problem with use)

F: Fair (less gloss)

P: Poor (there is no gloss)

<Transparency>

Ex: Excellent (there is no turbidity)

G: Good (there is slight turbidity, but there is no problem with use)

F: Fair (there is slight white turbidity)

P: Poor (white turbidity)

<Smoothness>

Ex: Excellent (there is no unevenness)

G: Good (there is slight unevenness, but there is no problem with use)

F: Fair (there is some unevenness)

P: Poor (there is cissing or unevenness on the whole surface)

Preparation Example 1 (Preparation of a Reaction Composition Solution (C-1) Including a Reaction Product of a Polyfunctional Liquid Epoxy Resin Having a Glycidyloxy Group Derived from Bisphenol A and Isophoronediamine)

1,022 g (6.0 mol) of isophoronediamine (IPDA) was charged into a separable flask having an inner volume of 2 liters equipped with a stirrer, a thermometer, a nitrogen introduction tube, a dropping funnel and a cooling tube, and the mixture was warmed to 80° C. while stirring the mixture under nitrogen flow. 372 g (1.0 mol) of a polyfunctional liquid epoxy resin having a glycidyloxy group derived from bisphenol A ("jER828", manufactured by Mitsubishi Chemical Corporation) was added dropwise thereto over 2 hours while maintaining the temperature at 80° C. After the completion of dropwise addition, a reaction composition including a reaction product of the epoxy resin and isophoronediamine was obtained by increasing the temperature to 100° C. and carrying out the reaction for 2 hours. A reaction composition solution (C-1) was obtained by adding benzyl alcohol to the reaction composition and diluting the reaction composition such that the concentration of the reaction composition was 56% by mass. The AHEW of the reaction composition solution (C-1) was 113.

Example 1 (Preparation of Water-Based Epoxy Resin Composition)

A water-based emulsion of a liquid epoxy resin having a glycidyloxy group derived from bisphenol A ("W2821R70" manufactured by Mitsubishi Chemical Corporation, epoxy equivalent weight in an emulsion state: 334 g/equivalent weight, epoxy resin concentration: 60% by mass, water content: 30% by mass, content of other components (emulsifier and the like): 10% by mass, and viscosity (25° C.): 700 mPa·s) was used as a main agent, and (A-1) GASKAMINE 240 (manufactured by Mitsubishi Gas Chemical Company, Inc., AHEW: 103) which is a reaction composition including a reaction product of styrene and metaxylylenediamine (MXDA) was used as a curing agent for a water-based epoxy resin. With 100 parts by mass of the main agent, the curing agent was blended at a ratio shown in Table 1, such that the number of active hydrogens in the curing agent and the number of epoxy groups in the water-based epoxy resin became equimolar, and stirred, thereby obtaining a water-based epoxy resin composition.

The evaluation was performed by using the obtained water-based epoxy resin composition. The results are shown in Table 1.

Example 2

A curing agent for a water-based epoxy resin was formulated by mixing (A-1) GASKAMINE 240 and (B-1) GASKAMINE 328 (manufactured by Mitsubishi Gas Chemical Company, Inc., ANEW: 55) which is a reaction composition including a reaction product of epichlorohydrin and MXDA at a mass ratio of 80:20. The evaluation was performed by formulating a water-based epoxy resin composition in the same manner as in Example 1 using the curing agent. The results are shown in Table 1.

Example 3

The evaluation was performed by formulating the curing agent for a water-based epoxy resin and the water-based epoxy resin composition in the same manner as in Example 2, except that in Example 2, (B-2) GASKAMINE 328S (manufactured by Mitsubishi Gas Chemical Company, Inc., ANEW: 70) which is a reaction composition including a reaction product of epichlorohydrin and MXDA was used instead of (B-1). The results are shown in Table 1.

Example 4

A curing agent for a water-based epoxy resin was formulated by mixing (A-1) GASKAMINE 240 and the reaction composition solution (C-1) obtained in Preparation Example 1 at a mass ratio of 50:50 (the mass ratio of (A-1) and the reaction composition ((C) component) obtained in Preparation Example 1 was 64:36). The evaluation was performed by formulating a water-based epoxy resin composition in the same manner as in Example 1 using the curing agent. The results are shown in Table 1.

Example 5

The evaluation was performed by formulating a curing agent for a water-based epoxy resin and a water-based epoxy resin composition in the same manner as in Example 2, except that in Example 2, the mass ratio of (A-1) and (B-1) in the curing agent for a water-based epoxy resin was changed into 50:50. The results are shown in Table 1.

Example 6

The evaluation was performed by formulating a curing agent for a water-based epoxy resin and a water-based epoxy resin composition in the same manner as in Example 3, except that in Example 3, the mass ratio of (A-1) and (B-2) in the curing agent for a water-based epoxy resin was changed into 50:50. The results are shown in Table 1.

Comparative Example 1

The evaluation was performed by formulating a water-based epoxy resin composition in the same manner as in Example 1, except that in Example 1, 80% by mass of an aqueous solution of (B-1) was used instead of (A-1) as the curing agent for a water-based epoxy resin. The results are shown in Table 1.

Comparative Example 2

The evaluation was performed by formulating a water-based epoxy resin composition in the same manner as in Example 1, except that in Example 1, 80% by mass of an aqueous solution of (B-2) was used instead of (A-1) as the curing agent for a water-based epoxy resin. The results are shown in Table 1.

Comparative Example 3

The evaluation was performed by formulating a water-based epoxy resin composition in the same manner as in Example 1, except that in Example 1, a commercially available polyamide amine-based curing agent for a water-based epoxy resin ("WD11M60" manufactured by Mitsubishi Chemical Corporation, solid content concentration: 60% by mass (butyl cellosolve solution), and ANEW: 732) was used instead of (A-1) as the curing agent for a water-based epoxy resin. The results are shown in Table 1.

TABLE 1

| | | | Example 1 | Example 2 | Example 3 | Example 4 | Example 5 | Example 6 |
|---|---|---|---|---|---|---|---|---|
| Composition | Water-based epoxy resin | | W2821R70 | | | | | |
| | Curing agent for epoxy resin | (A-1) G-240 (part by mass) | 100 | 80 | 80 | 50 | 50 | 50 |
| | | (B-1) G-328 (part by mass) | — | 20 | — | — | 50 | — |
| | | (B-2) G-328S (part by mass) | — | — | 20 | — | — | 50 |
| | | (C-1) Reaction composition solution in Preparation Example 1 (part by mass) | — | — | — | 50 **** | — | — |
| | | WD11M60 (part by mass) | — | — | — | — | — | — |
| | | AHEW | 103 | 88 | 94 | 108 | 72 | 83 |
| | | Curing agent viscosity (25° C./mPa · s) | 66 | 160 | 290 | 220 | 660 | 4,900 |

TABLE 1-continued

|   |   |   |   |   |   |   |   |
|---|---|---|---|---|---|---|---|
|  | MXDA content (% by mass) | <1 | 5.3 | <1 | <1 | 13.4 | <1 |
|  | Amount of curing agent blended in composition (part by mass) * | 30.8 | 26.3 | 28.2 | 58.0 | 21.5 | 25.0 |
| Content of water in composition (% by mass) |  | 22.9 | 23.7 | 23.4 | 22.7 | 24.7 | 24.0 |

Evaluation at 23° C. and 50% R.H.

| | | | | | | | |
|---|---|---|---|---|---|---|---|
| Curing rate | Set to Touch (hr) | 5.0 | 4.2 | 3.7 | 3.7 | 4.9 | 3.4 |
| | Dust Free (hr) | 8.6 | 8.8 | 8.0 | 7.1 | 12.7 | 12 |
| | Dry Through (hr) | >24 | >24 | >24 | >24 | >24 | >24 |

Test condition 1

| | |
|---|---|
| Finger contact drying (after 1/2/7 days) | Ex/Ex/Ex |
| Water resistance spot (after 1/2/7 days) | F/G/Ex |
| Pencil hardness (after 1/2/7 days) | F/H/H |
| Coating film appearance (glossiness/transparency/smoothness) | Ex/Ex/F |

Test condition 2

| | | | | | | |
|---|---|---|---|---|---|---|
| Finger contact drying (after 1/2/7 days) | Ex/Ex/Ex | Ex/Ex/Ex | Ex/Ex/Ex | Ex/Ex/Ex | G/Ex/Ex | Ex/Ex/Ex |
| Water resistance spot (after 1/2/7 days) | F/G/Ex | F/F/G | F/F/G | Ex/Ex/Ex | P/P/F | F/F/G |
| Pencil hardness (after 1/2/7 days) | F/H/H | H/H/H | H/H/H | H/H/H | F/H/H | H/H/H |

|   |   |   | Comparative Example 1 | Comparative Example 2 | Comparative Example 3 |
|---|---|---|---|---|---|
| Composition | Water-based epoxy resin | | | W2821R70 | |
|  | Curing agent for epoxy resin | (A-1) G-240 (part by mass) | — | — | — |
|  |  | (B-1) G-328 (part by mass) | 100 ** | — | — |
|  |  | (B-2) G-328S (part by mass) | — | 100 ** | — |
|  |  | (C-1) Reaction composition solution in Preparation Example 1 (part by mass) | — | — | — |
|  |  | WD11M60 (part by mass) | — | — | 100 |
|  |  | AHEW | 69 | 88 | 732 |
|  |  | Curing agent viscosity (25° C./mPa·s) | 1,200 ** | 12,100 ** | 4,400 |
|  |  | MXDA content (% by mass) | 21.4 | <1 | <1 |
|  |  | Amount of curing agent blended in composition (part by mass) * | 20.6 | 26.2 | 219 |
| Content of water in composition (% by mass) | | | 28.3 | 27.9 | 9.4 |

Evaluation at 23° C. and 50% R.H.

| | | | | |
|---|---|---|---|---|
| Curing rate | Set to Touch (hr) | 0.8 *** | >24 | 0.8 |
| | Dust Free (hr) | 1.5 *** | >24 | 4.7 |
| | Dry Through (hr) | >24 | >24 | >24 |

Test condition 1

| | | | |
|---|---|---|---|
| Finger contact drying (after 1/2/7 days) | P/P/P | P/P/P | Ex/Ex/Ex |
| Water resistance spot (after 1/2/7 days) | P/P/P | P/P/P | G/G/G |
| Pencil hardness (after 1/2/7 days) | <6B/<6B/<6B | <6B/<6B/<6B | 2B/B/B |
| Coating film appearance (glossiness/transparency/smoothness) | P/P/F | G/G/F | F/Ex/F |

Test condition 2

| | | | |
|---|---|---|---|
| Finger contact drying (after 1/2/7 days) | P/F/G | F/F/G | Ex/Ex/Ex |
| Water resistance spot (after 1/2/7 days) | P/P/P | P/P/P | Ex/Ex/Ex |
| Pencil hardness (after 1/2/7 days) | <6B/<6B/<F | <6B/<6B/<HB | 2B/2B/B |

1) The AHEW, viscosity and MXDA content of the curing agent, and the amount of curing agent blended in the composition In each of Example 4 and Comparative Examples 1 to 3 are values based on the curing agent solution
2) The hatched portion is not evaluated
* Part by mass of the curing agent (or the curing agent solution) based on 100 parts by mass of the epoxy resin emulsion which is a water-based epoxy resin
** Used in a state of 80% by mass of an aqueous solution
*** Production of carbonate
**** (C-1) was blended in an amount of 50 parts by mass of a benzyl alcohol solution having a reaction composition concentration of 56% by mass As shown in Table 1, as compared to the water-based epoxy resin compositions in Examples 1 to 6, which have good curability and excellent performance of the coating film, such as water resistance, hardness, and appearance, the water-based epoxy resin compositions in Comparative Examples 1 and 2 had a result that the finger contact drying, water resistance spot, pencil hardness, and coating film appearance deteriorated under either of the test conditions 1 and 2. In addition, in the water-based epoxy resin composition in Comparative Example 1, carbonate was precipitated on the surface of the coating film during the evaluation of the curing rate. Since the content of the MXDA in the curing agent was large, carbonate of the MXDA was produced.

In the water-based epoxy resin composition including the curing agent for a water-based epoxy resin in Comparative Example 3, the curing rate, finger contact drying, water resistance spot, and coating film appearance were good, but the pencil hardness of the coating film deteriorated. Furthermore, since the curing agent in Comparative Example 3 contains an organic solvent, there may be concern with environmental impact or safety in some cases.

Example 7

The evaluation was performed by formulating a water-based epoxy resin composition in the same manner as in Example 1, except that in a water-based emulsion of a solid epoxy resin having a glycidyloxy group derived from bisphenol A ("W1155R55" manufactured by Mitsubishi Chemical Corporation, epoxy equivalent weight in an emulsion state: 1,020 g/equivalent weight, epoxy resin concentration: 50% by mass, water content: 45% by mass, content of other components (emulsifier and the like): 5% by mass, and viscosity (25° C.): 500 mPa·s) was used instead of W2821R70 of Example 1 as the main agent. The results are shown in Table 2.

Example 8

A curing agent for a water-based epoxy resin was formulated by mixing (A-1) GASKAMINE 240 and (B-1) GASKAMINE 328 (manufactured by Mitsubishi Gas Chemical Company, Inc.) which is a reaction composition including a reaction product of epichlorohydrin and MXDA at a mass ratio of 80:20. The evaluation was performed by formulating a water-based epoxy resin composition in the same manner as in Example 7 using the curing agent. The results are shown in Table 2.

Example 9

The evaluation was performed by formulating a curing agent for a water-based epoxy resin and a water-based epoxy resin composition in the same manner as in Example 8, except that in Example 8, (B-2) GASKAMINE 328S (manufactured by Mitsubishi Gas Chemical Company, Inc.) which is a reaction composition including a reaction product of epichlorohydrin and MXDA was used instead of (B-1). The results are shown in Table 2.

Example 10

A curing agent for a water-based epoxy resin was formulated by mixing (A-1) GASKAMINE 240 and the reaction composition solution (C-1) obtained in Preparation Example 1 at a mass ratio of 50:50 (the mass ratio of (A-1) and the reaction composition ((C) component) obtained in Preparation Example 1 was 64:36). The evaluation was performed by formulating a water-based epoxy resin composition in the same manner as in Example 7 using the curing agent. The results are shown in Table 2.

Comparative Example 4

The evaluation was performed by formulating a water-based epoxy resin composition in the same manner as in Example 7, except that in Example 7, 80% by mass of an aqueous solution of (B-1) was used instead of (A-1) as the curing agent for a water-based epoxy resin. The results are shown in Table 2.

Comparative Example 5

The evaluation was performed by formulating a water-based epoxy resin composition in the same manner as in Example 7, except that in Example 7, 80% by mass of an aqueous solution of (B-2) was used instead of (A-1) as the curing agent for a water-based epoxy resin. The results are shown in Table 2.

Comparative Example 6

The evaluation was performed by formulating a water-based epoxy resin composition in the same manner as in Example 7, except that in Example 7, a commercially available polyamide amine-based curing agent for a water-based epoxy resin ("WD11M60" manufactured by Mitsubishi Chemical Corporation, solid content concentration: 60% by mass (butyl cellosolve solution), and ANEW: 732) was used instead of (A-1) as the curing agent for a water-based epoxy resin. The results are shown in Table 2.

TABLE 2

| | | | Example 7 | Example 8 | Example 9 | Example 10 |
|---|---|---|---|---|---|---|
| Composition | Water-based epoxy resin | | W1155R55 | | | |
| | Curing agent for epoxy resin | (A-1) G-240 (part by mass) | 100 | 80 | 80 | 50 |
| | | (B-1) G-328 (part by mass) | — | 20 | — | — |
| | | (B-2) G-328S (part by mass) | — | — | 20 | — |
| | | (C-1) Reaction composition solution in Preparation Example 1 (part by mass) | — | — | — | 50 **** |
| | | WD11M60 (part by mass) | — | — | — | — |
| | | AHEW | 103 | 88 | 94 | 108 |
| | | Curing agent viscosity (25° C./mPa · s) | 66 | 160 | 290 | 220 |
| | | MXDA content (% by mass) | <1 | 5.3 | <1 | <1 |
| | | Amount of curing agent blended in composition (part by mass) * | 10.1 | 8.6 | 9.2 | 10.6 |
| Content of water in composition (% by mass) | | | 40.9 | 41.4 | 41.2 | 40.7 |
| Evaluation at 23° C. and 50% R.H. | | | | | | |
| Curing rate | Set to Touch (hr) | | 0.1 | 0.1 | 0.1 | 0.1 |
| | Dust Free (hr) | | 1.3 | 1.2 | 1.1 | 1.8 |
| | Dry Through (hr) | | 6.4 | 3.8 | 3.5 | 9.0 |

TABLE 2-continued

| Test condition 1 | | | | |
|---|---|---|---|---|
| Finger contact drying (after 1/2/7 days) | Ex/Ex/Ex | | | |
| Water resistance spot (after 1/2/7 days) | Ex/Ex/Ex | | | |
| Pencil hardness (after 1/2/7 days) | H/H/H | | | |
| Coating film appearance (glossiness/transparency/smoothness) | Ex/Ex/F | | | |
| Test condition 2 | | | | |
| Finger contact drying (after 1/2/7 days) | Ex/Ex/Ex | Ex/Ex/Ex | Ex/Ex/Ex | Ex/Ex/Ex |
| Water resistance spot (after 1/2/7 days) | Ex/Ex/Ex | G/G/G | G/G/G | Ex/Ex/Ex |
| Pencil hardness (after 1/2/7 days) | H/H/H | H/H/H | H/H/H | H/H/H |

| | | | Comparative Example 4 | Comparative Example 5 | Comparative Example 6 |
|---|---|---|---|---|---|
| Composition | Water-based epoxy resin | | | W1155R55 | |
| | Curing agent for epoxy resin | (A-1) G-240 (part by mass) | — | — | — |
| | | (B-1) G-328 (part by mass) | 100 ** | — | — |
| | | (B-2) G-328S (part by mass) | — | 100 ** | — |
| | | (C-1) Reaction composition solution in Preparation Example 1 (part by mass) | — | — | — |
| | | WD11M60 (part by mass) | — | — | 100 |
| | | AHEW | 69 | 88 | 732 |
| | | Curing agent viscosity (25° C./mPa · s) | 1,200 ** | 12,100 ** | 4,400 |
| | | MXDA content (% by mass) | 21.4 | <1 | <1 |
| | | Amount of curing agent blended in composition (part by mass) * | 6.8 | 8.6 | 71.8 |
| Content of water in composition (% by mass) | | | 42.1 | 41.4 | 26.2 |
| Evaluation at 23° C. and 50% R.H. | | | | | |
| Curing rate | Set to Touch (hr) | | 0.1 | 0.1 | 0.7 |
| | Dust Free (hr) | | 0.9 | 0.5 | 4.0 |
| | Dry Through (hr) | | 2.1 | 1.3 | >24 |
| Test condition 1 | | | | | |
| Finger contact drying (after 1/2/7 days) | | | Ex/Ex/Ex | Ex/Ex/Ex | Ex/Ex/Ex |
| Water resistance spot (after 1/2/7 days) | | | P/P/P | P/P/P | G/G/Ex |
| Pencil hardness (after 1/2/7 days) | | | H/H/H | HB/H/H | <6B/B/H |
| Coating film appearance (glossiness/transparency/smoothness) | | | P/P/P *** | P/P/P *** | P/Ex/F |
| Test condition 2 | | | | | |
| Finger contact drying (after 1/2/7 days) | | | Ex/Ex/Ex | Ex/Ex/Ex | Ex/Ex/Ex |
| Water resistance spot (after 1/2/7 days) | | | F/F/F | F/F/F | G/G/Ex |
| Pencil hardness (after 1/2/7 days) | | | H/H/H | H/H/H | B/H/H |

1) The AHEW, viscosity and MXDA content of the curing agent, and the amount of curing agent blended in the composition in each of Example 10 and Comparative Examples 4 to 6 are values based on the curing agent solution
2) The hatched portion is not evaluated
* Part by mass of the curing agent (or the curing agent solution) based on 100 parts by mass of the epoxy resin emulsion which is a water-based epoxy resin
** Used in a state of 80% by mass of an aqueous solution
*** White turbid until 2 days passed
*** (C-1) was blended in an amount of 50 parts by mass of a benzyl alcohol solution having a reaction composition concentration of 56% by mass As shown in Table 2, as compared to the water-based epoxy resin compositions in Examples 7 to 10, which have good curability and excellent performance of the coating film, such as water resistance, hardness, and appearance, in the water-based epoxy resin compositions in Comparative Examples 4 and 5, the water resistance spot of the coating film and the coating film appearance deteriorated under either of the test conditions 1 and 2. In the water-based epoxy resin composition containing the curing agent for a water-based epoxy resin in Comparative Example 6, the pencil hardness of the coating film deteriorated under either of the test conditions 1 and 2, and particularly, the pencil hardness deteriorated under the test condition 1.

The components used in Tables 1 and 2 are shown below.
<Water-Based Epoxy Resin>
W2821R70:
Water-based emulsion (manufactured by Mitsubishi Chemical Corporation, epoxy equivalent weight in an emulsion state: 334 g/equivalent weight, epoxy resin concentration: 60% by mass, water content: 30% by mass, content of other components (emulsifier, and the like): 10% by mass, and viscosity (25° C.): 700 mPa·s) of a liquid epoxy resin having a glycidyloxy group derived from bisphenol A W1155R55:
Water-based emulsion (manufactured by Mitsubishi Chemical Corporation, epoxy equivalent weight in an emulsion state: 1,020 g/equivalent weight, epoxy resin concentration: 50% by mass, water content: 45% by mass, content of other components (emulsifier, and the like): 5% by mass, and viscosity (25° C.): 500 mPa·s) of a solid epoxy resin having a glycidyloxy group derived from bisphenol A
<Curing Agent Components for Water-Based Epoxy Resin>
(A-1):
GASKAMINE 240 (a reaction composition including a reaction product of styrene and MXDA, manufactured by Mitsubishi Gas Chemical Company, Inc., content of the reaction product of styrene and MXDA: >99% by mass, content of MXDA: <1% by mass, content of a compound represented by the following formula (2-1): 49% by mass, and AHEW: 103)

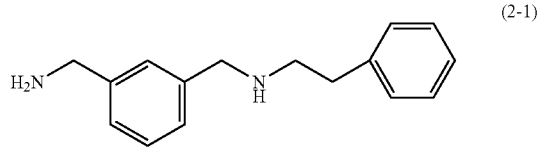 [SMILES: NCc1cccc(CNCCc2ccccc2)c1]

(2-1)

(B-1):
GASKAMINE 328 (a reaction composition including a reaction product of epichlorohydrin and MXDA, manufactured by Mitsubishi Gas Chemical Company, Inc., content of MXDA: 26.7% by mass, content of a compound represented by the following formula (3-1): 73.3% by mass (n is a number of 1 to 12 and content of a compound with n=1 is 20.9% by mass in (B-1)), and AHEW: 55)

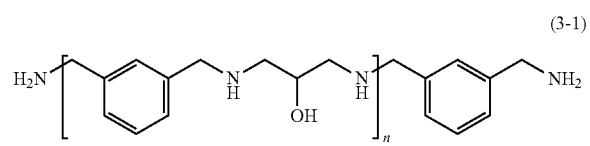

(3-1)

(B-2):
GASKAMINE 328S (a reaction composition including a reaction product of epichlorohydrin and MXDA, manufactured by Mitsubishi Gas Chemical Company, Inc., content of MXDA: 0.9% by mass, content of the compound represented by the formula (3-1): 99.1% by mass (n is a number of 1 to 12 and content of a compound with n=1 is 29.3% by mass in (B-2)), and AHEW: 70)

(C-1):
Reaction composition solution (concentration of the reaction composition: 56% by mass, AHEW of the benzyl alcohol solution and the reaction composition solution: 113) including a reaction product of a polyfunctional epoxy resin having a glycidyloxy group derived from bisphenol A and isophoronediamine, which is obtained in Preparation Example 1

WD11M60:
Polyamide amine-based curing agent for a water-based epoxy resin (manufactured by Mitsubishi Chemical Corporation, solid content concentration: 60% by mass (butyl cellosolve solution), and AHEW: 732)

Example 11 (Preparation of Water-Based Epoxy Resin Composition)

A polyfunctional liquid epoxy resin "jER828" having a glycidyloxy group derived from bisphenol A (manufactured by Mitsubishi Chemical Corporation, epoxy equivalent weight: 186 g/equivalent weight) was used as an epoxy resin, polyoxyethylene styrenated phenyl ether "NOIGEN EA-207D" (manufactured by Daiichi Kogyo Seiyaku Co., Ltd., HLB: 12.7) was used as an emulsifier, and (A-1) GASKAMINE 240 (manufactured by Mitsubishi Gas Chemical Company, Inc., ANEW: 103) which is a reaction composition including a reaction product of styrene and metaxylylenediamine (MXDA) was used as a curing agent for a water-based epoxy resin.

28 g of the epoxy resin jER828, 2.8 g of the emulsifier, and 15.5 g of the curing agent for a water-based epoxy resin (A-1) were blended, and the resulting mixture was stirred at a rotation speed of 500 rpm for 1 minute by DISPER (manufactured by Primix Corporation, Homodisper 2.5 type). 2 g of pure water was added thereto, an operation of stirring the mixture at a rotation speed of 500 rpm for 1 minute by DISPER was performed 10 times, and a total of 20 g of pure water was added thereto to obtain a water-based epoxy resin composition. The evaluation under the test condition 1 was performed by using the water-based epoxy resin composition. The results are shown in Table 3.

Example 12

The evaluation under the test condition 1 was performed by formulating a water-based epoxy resin composition in the same manner as in Example 11, except that in Example 11, polyoxyethylene styrenated phenyl ether "BLAUNON KTSP-16" (manufactured by Aoki Oil Industrial Co., Ltd., HLB: 18.7) was used instead of "NOIGEN EA-207D" as an emulsifier. The results are shown in Table 3.

Example 13

In Example 11, a polymer emulsifier containing an epoxy group and a hydrophilic group, "MARPROOF GP-013023" (manufactured by NOF Corporation, epoxy equivalent weight: 535 g/equivalent weight, and HLB: 10.9) was used instead of "NOIGEN EA-207D" as an emulsifier. 28 g of the epoxy resin jER828, 2.8 g of the emulsifier, and 16.0 g of the curing agent for a water-based epoxy resin (A-1) were blended, and the resulting mixture was stirred at a rotation speed of 500 rpm for 1 minute by DISPER. 2 g of pure water was added thereto, an operation of stirring the mixture at a rotation speed of 500 rpm for 1 minute by DISPER was performed 10 times, and a total of 20 g of pure water was added thereto to obtain a water-based epoxy resin composition. The evaluation under the test condition 1 was performed by using the water-based epoxy resin composition. The results are shown in Table 3.

Example 14

(Preparation of Curing Agent Mixture for Water-Based Epoxy Resin)
Polyoxyethylene styrenated phenyl ether "NOIGEN EA-207D" (manufactured by Daiichi Kogyo Seiyaku Co., Ltd., HLB: 12.7) was used as an emulsifier, and (A-1) GASKAMINE 240 (manufactured by Mitsubishi Gas Chemical Company, Inc., ANEW: 103) which is a reaction composition including a reaction product of styrene and metaxylylenediamine (MXDA) was used as a curing agent for a water-based epoxy resin.

2.8 g of the emulsifier and 15.5 g of the curing agent for a water-based epoxy resin (A-1) were blended and the resulting mixture was stirred at a rotation speed of 500 rpm for 1 minute by DISPER to obtain a curing agent mixture for a water-based epoxy resin.
(Preparation of Water-Based Epoxy Resin Composition)
28 g of an epoxy resin "jER828" (a liquid epoxy resin, manufactured by Mitsubishi Chemical Corporation) was blended with the curing agent mixture for a water-based epoxy resin, and the resulting mixture was stirred at a rotation speed of 500 rpm for 1 minute by DISPER (manufactured by Primix Corporation, Homodisper 2.5 type). 2 g of pure water was added thereto, an operation of stirring the mixture at a rotation speed of 500 rpm for 1 minute by DISPER was performed 10 times, and a total of 20 g of pure water was added thereto to obtain a water-based epoxy resin composition. The evaluation under the test condition 1 was performed by using the water-based epoxy resin composition. The results are shown in Table 3.

TABLE 3

|  |  |  |  | Example 11 | Example 12 | Example 13 | Example 14 *** |
|---|---|---|---|---|---|---|---|
| Composition | Water-based epoxy resin (part by mass) * | Epoxy resin | jER828 | 55.1 | 55.1 | 55.1 | 55.1 |
|  |  | Emulsifier (part by mass) * | NOIGEN EA-207D | 5.5 |  |  | 5.5 |
|  |  |  | BLAUNON KTSP-16 |  | 5.5 |  |  |
|  |  |  | MARPROOF GP-013023 |  |  | 5.5 |  |
|  |  | Water (part by mass) * |  | 39.4 | 39.4 | 39.4 | 39.4 |
|  |  | Epoxy equivalent weight in an emulsion state (g/equivalent weight) |  | 337 | 337 | 327 | 337 |
|  | Curing agent for epoxy resin (part by mass) ** | (A-1) G-240 |  | 30.5 | 30.5 | 31.5 | 30.5 |
| Content of water in composition (% by mass) |  |  |  | 30.2 | 30.2 | 30.2 | 30.2 |
| Evaluation at 23° C. and 50% R.H. |  |  |  |  |  |  |  |
| Curing rate |  | Set to Touch (hr) |  | 4:30 | 4:00 | 4:00 | 1:45 |
|  |  | Dust Free (hr) |  | 5:45 | 6:45 | 7:00 | 4:30 |
|  |  | Dry Through (hr) |  | 16:15 | 15:00 | 17:15 | 8:30 |
| Test condition 1 |  |  |  |  |  |  |  |
| Finger contact drying (after 1/2/7 days) |  |  |  | Ex/Ex/Ex | Ex/Ex/Ex | Ex/Ex/Ex | Ex/Ex/Ex |
| Water resistance spot (after 1/2/7 days) |  |  |  | Ex/Ex/Ex | Ex/Ex/Ex | Ex/Ex/Ex | Ex/Ex/Ex |
| Pencil hardness (after 1/2/7 days) |  |  |  | H/H/H | H/H/H | H/H/H | H/H/H |
| Coating film appearance (glossiness/transparency/smoothness) |  |  |  | Ex/Ex/G | Ex/Ex/G | Ex/Ex/P | Ex/Ex/F |

* Part by mass in 100 parts by mass of water-based epoxy resin (epoxy resin + emulsifier + water)
** Part by mass based on 100 parts by mass of the water-based epoxy resin
*** Using a curing agent mixture for a water-based epoxy resin The components used in Table 3 are shown below.
<Water-Based Epoxy Resin Components>
[Epoxy Resin]
jER828:
Polyfunctional liquid epoxy resin having a glycidyloxy group derived from bisphenol A (manufactured by Mitsubishi Chemical Corporation, epoxy equivalent weight: 186 g/equivalent weight)
[Emulsifier]
NOIGEN EA-207D:
Polyoxyethylene styrenated phenyl ether (manufactured by Daiichi Kogyo Seiyaku Co., Ltd., HLB: 18.7)
BLAUNON KTSP-16:
Polyoxyethylene styrenated phenyl ether (manufactured by Aoki Oil Industrial Co., Ltd., HLB: 12.7)
MARPROOF GP-013023:
Polymer emulsifier containing an epoxy group and a hydrophilic group (manufactured by NOF Corporation, epoxy equivalent weight: 535 g/equivalent weight, HLB: 10.9)
<Curing Agent Components for Water-Based Epoxy Resin>
(A-1):
GASKAMINE 240 (a reaction composition including a reaction product of styrene and MXDA, manufactured by Mitsubishi Gas Chemical Company, Inc., content of the reaction product of styrene and MXDA: >99% by mass, content of MXDA: <1% by mass, content of the compound represented by the formula (2-1): 49% by mass, and ANEW: 103)

As shown in Table 3, the water-based epoxy resin compositions in Examples 11 to 14 have good curability and excellent performance of the coating film, such as water resistance, hardness, and appearance.

INDUSTRIAL APPLICABILITY

By using the curing agent for a water-based epoxy resin of the present invention, it is possible to provide a water-based epoxy resin composition which does not contain a solvent, is also suitable in terms of environment or safety, has good curability, and is also excellent in coating film performance such as water resistance, hardness, and appearance. The water-based epoxy resin composition provides a cured product having good properties, and thus is suitably used for various paints such as a paint for corrosion resistance, an adhesive, a floor material, a sealant, a polymer cement mortar, a gas barrier coating, a primer, a screed, a topcoat, a sealing material, a crack repair material, a road paving material, and the like in addition to the use in a concrete material.

The invention claimed is:
1. A water-based epoxy resin composition comprising
a water-based epoxy resin comprising an epoxy resin emulsion in which an epoxy resin having a glycidyloxy group derived from bisphenol A is emulsified and dispersed in water;
a curing agent for the water-based epoxy resin comprising a curing agent component comprising a reaction composition (A) comprising a reaction product of styrene and an amine compound represented by the following formula (1):

$$H_2N-CH_2\text{-A-}CH_2-NH_2 \quad (1)$$

wherein A is a 1,2-phenylene group, a 1,3-phenylene group, or a 1,4-phenylene group;
wherein the content of the reaction composition (A) in the curing agent for the water-based epoxy resin is 85% by mass or more;
wherein content of the curing agent in the water-based epoxy resin composition is an amount in which the ratio of the number of active hydrogens in the curing agent to the number of epoxy groups in the water-based epoxy resin is 1/0.8 to 1/1.2; and wherein a total amount of the curing agent component and the epoxy resin having a glycidyloxy group derived from bisphenol A in the epoxy resin composition is 52.7% by mass or more.

2. The water-based epoxy resin composition according to claim 1, wherein the reaction composition (A) contains 10 mass % or more of a compound represented by the following formula (2):

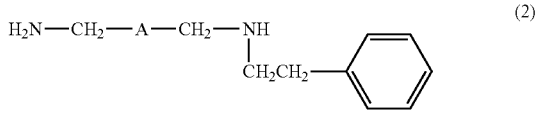
(2)

wherein A is the same as defined above.

3. The water-based epoxy resin composition according to claim 1, wherein A is a 1,3-phenylene group.

4. The water-based epoxy resin composition according to claim 1, further comprising a reaction composition comprising a reaction product of a compound having at least one epoxy group in a molecule thereof and a polyamine compound.

5. The water-based epoxy resin composition according to claim 4, wherein the reaction composition is a reaction composition (B) comprising a reaction product of epichlorohydrin and the amine compound represented by the formula (1).

6. The water-based epoxy resin composition according to claim 5, wherein the reaction composition (B) comprises, as a main component, a compound represented by the following formula (3):

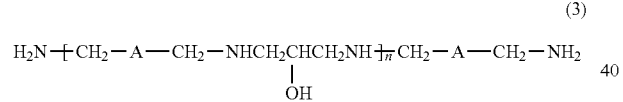
(3)

wherein A is the same as defined above, and n is a number of 1 to 12.

7. The water-based epoxy resin composition according to claim 4, wherein the reaction composition is a reaction composition (C) comprising a reaction product of a compound having at least two epoxy groups in a molecule thereof and a polyamine compound.

8. The water-based epoxy resin composition according to claim 1, wherein the water-based epoxy resin is an epoxy resin emulsion comprising the epoxy resin having a glycidyloxy group derived from bisphenol A, an emulsifier, and water.

9. The water-based epoxy resin composition according to claim 8, wherein a hydrophile-lipophile balance (HLB) of the emulsifier defined by a Griffin method is from 8.0 to 20.0.

10. The water-based epoxy resin composition according to claim 8, wherein the emulsifier is one or more selected from the group consisting of polyoxyalkylene aryl ether and polyoxyalkylene alkyl aryl ether.

11. A cured product of the water-based epoxy resin composition according to claim 1.

12. A water-based epoxy resin composition comprising a water-based epoxy resin comprising an epoxy resin emulsion in which an epoxy resin having a glycidyloxy group derived from bisphenol A is emulsified and dispersed in water;

a curing agent for the water-based epoxy resin comprising a curing agent component comprising a reaction composition (A) comprising a reaction product of styrene and an amine compound represented by the following formula (1):

$H_2N-CH_2\text{-}A\text{-}CH_2-NH_2$ (1)

wherein A is a 1,2-phenylene group, a 1,3-phenylene group, or a 1,4-phenylene group;

a reaction composition (C) comprising a reaction product of isophoronediamine and a polyfunctional epoxy resin having a glycidyloxy group derived from bisphenol A;

wherein the content of the reaction composition (A) in the curing agent for the water-based epoxy resin is 85% by mass or more, wherein content of the curing agent in the water-based epoxy resin composition is an amount in which the ratio of the number of active hydrogens in the curing agent to the number of epoxy groups in the water-based epoxy resin is 1/0.8 to 1/1.2, and wherein a total amount of the curing agent component and the epoxy resin having a glycidyloxy group derived from bisphenol A in the epoxy resin composition is 52.7% by mass or more.

* * * * *